United States Patent [19]

Laanio et al.

[11] Patent Number: 4,563,457

[45] Date of Patent: Jan. 7, 1986

[54] SYNERGISTIC PESTICIDAL COMPOSITIONS COMPRISING 2,4-DIAMINO-6-CYCLOPROPYLAMINO-S-TRIAZINE AND CYPERMETHRIN

[75] Inventors: Verena Laanio, Arisdorf; Marcus von Orelli, Münchenstein; Walter Häusermann, Ollon, all of Switzerland

[73] Assignee: Ciba Geigy Corporation, Ardsley, N.Y.

[21] Appl. No.: 501,458

[22] Filed: Jun. 6, 1983

Related U.S. Application Data

[63] Continuation-in-part of Ser. No. 321,843, Nov. 16, 1981, abandoned.

[30] Foreign Application Priority Data

Nov. 25, 1980 [CH] Switzerland ............... 8707/80
Nov. 25, 1980 [CH] Switzerland ............... 8704/80

[51] Int. Cl.[4] ................. A01N 43/64; A01N 37/34
[52] U.S. Cl. ................. 514/245; 514/521
[58] Field of Search ............... 424/249, 304; 514/245, 514/521

[56] References Cited

U.S. PATENT DOCUMENTS

| 4,206,227 | 6/1980 | Mues et al. | 424/225 |
|---|---|---|---|
| 4,225,598 | 9/1980 | Brechbühler et al. | 424/249 |
| 4,257,987 | 3/1981 | Arend et al. | 424/219 |
| 4,308,262 | 12/1981 | Badmin et al. | 424/304 |
| 4,312,816 | 1/1982 | Aketa et al. | 424/304 |
| 4,321,212 | 3/1982 | Suzuki et al. | 424/304 |
| 4,346,092 | 8/1982 | Sanborn | 424/304 |

FOREIGN PATENT DOCUMENTS

| 857896 | 2/1978 | Belgium . |
| 2805226 | 8/1978 | Fed. Rep. of Germany . |
| 1439615 | 6/1976 | United Kingdom . |

OTHER PUBLICATIONS

Borkovec et al., "Insect Chemosterilants V. Derivatives of Melamine", J. Med. Chem. 10 (1967), pp. 457-461.
Elliott et al., "A Photostable Pyrethroid", Nature, vol. 246 (1973), pp. 169-170.
Pesticide Manual, 6th Ed. (1979), pp. 143-144.
Abstract, Japanese Kokai 73-52937, Chem. Abstr. 79, 122576u (1973).

Primary Examiner—Jerome D. Goldberg
Assistant Examiner—John M. Kilcoyne
Attorney, Agent, or Firm—Edward McC. Roberts; Frederick H. Rabin

[57] ABSTRACT

The invention relates to insecticidal and acaricidal compositions which contain a synergistic combination of the compounds 2,4-Diamino-6-cyclopropylamino-s-triazine and (RS)-α-cyano-3-phenoxybenzyl(1RS)-cis,trans-3-(2,2-dichlorovinyl)-2,2-dimethylcyclopropanecarboxylate.

2 Claims, No Drawings

SYNERGISTIC PESTICIDAL COMPOSITIONS COMPRISING 2,4-DIAMINO-6-CYCLOPROPYLAMINO-S-TRIAZINE AND CYPERMETHRIN

CROSS REFERENCE TO RELATED APPLICATION

This is a continuation-in-part of application Ser. No. 321,843, filed Nov. 16, 1981, now abandoned.

DETAILED DISCLOSURE

The present invention relates to novel insecticidal and acaricidal compositions which contain an active ingredient combination, together with one or more inert adjuvants, and to the use of said combination, or of a composition containing it, for controlling insects and mites of the order Acarina.

The control of pests is increasingly giving rise to serious problems which involve environmental pollution on the one hand, and the development of resistance on the other. Although a wide range of pesticides is available, increasing environmental pollution puts a limit to the use of chemical substances. However, if there is no longer any guarantee of the total destruction of a pest population, including its various development stages, as a consequence of low rates of application, then the development of resistance to the chemicals employed is promoted. This resistance leads to the build-up of pest populations which are not adequately controlled, or which can no longer be controlled at all, by the compounds originally employed. Resistance can be built up not only to individual compounds, but also to classes of compounds. It is therefore desirable in pest control to use compositions which hinder the development of resistance when employed in environmentally tolerable rates of application.

Accordingly, it is an object of the present invention to provide compositions for controlling insects and mites of the order Acarina, in particular parasitic mites and, most particularly, mites which are parasites of animals, with which compositions pests are effectively controlled using environmentally tolerable rates of application, while substantially avoiding the development of resistance.

The compositions of the present invention contain an active ingredient combination which consists of the compound 2,4-diamino-6-cyclopropylamino-s-triazine of the formula Ia

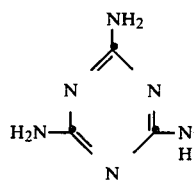
(Ia)

and the compound (RS)-α-cyano-3-phenoxybenzyl (1RS)-cis,trans-3-(2,2-dichlorovinyl)-2,2-dimethylcyclopropanecarboxylate of the formula IIe

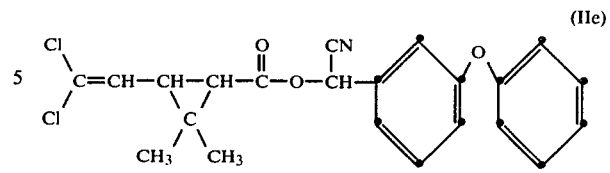
(IIe)

The individual compounds of which the active ingredient combination is composed are known pesticides and can be prepared by known methods.

The compound of the formula Ia, is described in Belgian patent specification No. 857 896. The formula IIe is disclosed in the Pesticide Manual, 6th Ed., 1979, and is known as cypermethrin.

Surprisingly, it has now been found that the active ingredient combination in the compositions of the invention displays synergistic activity i.e. that it significantly exceeds the additive effect of the individual components.

The weight ratio of the compound of the formula Ia to the compound of the formula IIe in the synergistically effective ingredient combinations of the invention is in the range of 1:10 to 10:1. This weight ratio range is to be understood as being an average which can vary by ±10%.

The invention is illustrated by the following Example. The determination of the synergistic effect is carried out by the method of Y. P. Sun and E. R. Johnson for determining the biocidal activity of compound mixtures on specific species [J. Econ. Entomol. 53, 887 (1960)]. In this method, the synergistic effect of the combination of active ingredients is determined by comparing the dose/action curves of the combinations and their individual components, using the co-toxicity indices, and is calculated as follows:

$$\text{co-toxicity index } CI = \frac{IR_{50} \text{ theory}}{IR_{50} \text{ test}}.$$

In this equation, $IR_{50}$ denotes the concentration of the active ingredients, or combinations thereof, in µg/ml at which no reproduction of 50% of the test organisms takes place.

The theoretical $IR_{50}$ value expected of an active ingredient combination is based on the assumption of an additive effect of both the individual components and is calculated by the formula of the harmonic mean:

$$IR_{50} \text{ theory} = \frac{1}{\frac{a}{IR_{50}A} + \frac{b}{IR_{50}B}},$$

wherein a is the proportion of compound A and b the proportion of compound B, relative to the total weight of the combination A+B.

Active ingredient combinations with a synergistic, i.e. more than additive, action of the two individual components give co-toxicity indices with values of >1.

EXAMPLE 1

Fully replete ticks (*Boophilus microplus* + +) of the organophosphorus-resistant strain Biarra, in groups of 40, are fixed in the dorsal position in Petri dishes of 9 cm diameter and treated with freshly prepared solutions or suspensions of the active ingredients and of active ingredient combinations in standard WHO water. Sufficient liquid is poured into each dish that the ticks are completely immersed. After 1 hour the liquid is poured off and any drops still remaining are shaken off. The Petri dishes with the ticks are then dried overnight at room temperature and subsequently incubated for 4 weeks at 28° C. and 80% relative humidity until oviposition has taken place and the larvae have hatched out.

The criteria used for evaluating the activity of the tested compounds and compound mixtures are: the mortality and sterility of the treated femal ticks as well as the inability of the eggs to hatch. These effects are used to evaluate the inhibition of reproduction (IR).

A dilution series at different concentrations is used for each active ingredient or combination of active ingredients, and the corresponding dose/action curves and the $IR_{50}$ are determined by the method of Berkson (J. Am. Stat. Assoc. 48, 565, 1953).

The co-toxicity values are then determined from the values obtained for $IR_{50}$ test and $IR_{50}$ theory (Table 1). Combinations of compounds of the formulae Ia and IIe are tested.

TABLE 1

| Compound/ compound mixture | Weight ratio of the mixture | $IR_{50}$ test μg/ml | $IR_{50}$ theory μg/ml | Cotox. index |
| --- | --- | --- | --- | --- |
| Ia | — | >>15000 | — | — |
| IIe | — | 18.8 | — | — |
| Ia:IIe | 9:1 | 137.6 | 185.9 | 1.35 |
| Ia:IIe | 1:1 | 30.7 | 37.6 | 1.22 |
| Ia:IIe | 1:9 | 15.1 | 20.9 | 1.38 |

For controlling insects and mites of the order Acarina, the active ingredient combinations can be used by themselves or in the form of compositions which contain an active ingredient combination together with one or more inert adjuvants. Suitable inert adjuvants are solid and liquid, natural or regenerated substances conventionally employed in the art of formulation, e.g. solvents, dispersants, wetting agents, tackifiers, thickeners or binders.

The active ingredient combinations can be processed to formulations such as dusts, emulsifiable concentrates, granulates, dispersions, sprays, solutions or suspensions. It is also possible to use liquid, in particular, aqueous preparations or concentrates of active ingredient combinations for plunge dips, spray races, pour-on-solutions and manual methods of application (handspray and hand-dressing).

The compositions of the present invention are conveniently prepared by intimately mixing and/or grinding the active ingredient combinations with suitable adjuvants, with or without the addition of dispersants or solvents which are inert to the active ingredients. The active ingredient combinations can be processed e.g. to the following formulations:
solid formulations:
  dusts, tracking powders, granulates;
liquid formulations:
  (a) solutions,
  (b) water-dispersible concentrates of the active ingredient combinations: wettable powders, pastes, emulsions.

The compositions of the invention advantageously contain 2 to 80% by weight, preferably 5 to 50% by weight, of active ingredient combination.

EXAMPLE 2

Wettable powder

The following ingredients are intensively mixed in a mixing apparatus: 5 to 50 parts of an active ingredient combination, 5 parts of an absorbent carrier (silica gel K 320 or Wessalon S), 35 to 80 parts by weight of a carrier (Bolus alba or kaolin B 24) and a dispersing agent mixture consisting of 5 parts of a sodium laurylsulfonate and 5 parts of an alkylaryl polyglycol ether. This mixture is ground to a granular size of 5–15 μm in a disc attrition mill or air jet mill. The resultant wettable powder gives a good suspension in water.

EXAMPLE 3

Dust

The following ingredients are intensively mixed: 5 parts by weight of a finely ground active ingredient combination, 3 parts by weight of precipitated silic acid, and 92 parts by weight of talc.

The active ingredient combinations and the compositions containing them have a pronounced activity against insects and against mites of the order Acarina, especially those forms which are parasites of animals. They are particularly effective against ticks and against insects of the order Diptera, in which connection their excellent action against Diptera belonging to the family Calliphoridae merits special mention. It is especially the larvae of these insects which can cause severe damage in animal husbandry and their control is consequently of the first importance. Most particularly, attention is drawn to the very good efficiency of the active ingredient combinations of the compositions containing them in controlling representatives of the Lucilia belonging to the family Calliphoridae, especially of the species *Lucilia cuprina* and *Lucilia sericata* (blowflies).

What is claimed is:

1. A synergistic composition for controlling insects of the order Diptera and mites of the order Acarina, which composition comprises the compound 2,4-Diamino-6-cyclopropylamino-s-triazine of the formula Ia

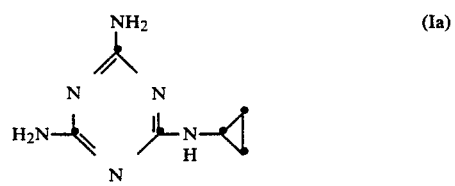

and the compound (RS)-α-cyano-3-phenoxybenzyl (1RS)-cis,trans-3-(2,2-dichlorovinyl)-2,2-dimethylcyclopropanecarboxylate of the formula IIe

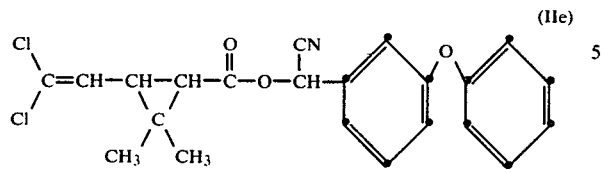
(IIe)

in which the ratio by weight of the compound of formula Ia to the compound of formula IIe in the active ingredient combination is from about 9:1 to about 1:9.

2. A method for controlling ticks which comprises contacting said ticks with an effective amount of a composition which comprises the compound 2,4-diamino-6-cyclopropyl-amino-s-triazine of the formula Ia

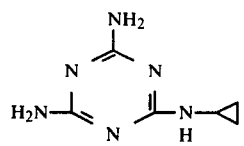
(Ia)

and the compound (RS)-α-cyano-3-phenoxybenzyl (1RS)-cis,trans-3-(2,2-dichlorovinyl)-2,2-dimethylcyclopropanecarboxylate of the formula IIe

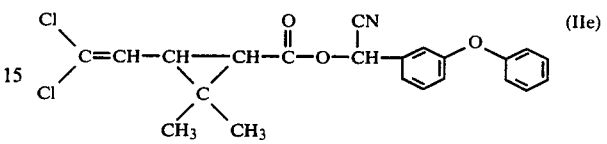
(IIe)

in which the ratio by weight of the compound of formula Ia to the compound of formula IIe in the active ingredient combination is from about 9:1 to about 1:9.

* * * * *